(12) United States Patent
Chiu et al.

(10) Patent No.: US 9,717,808 B2
(45) Date of Patent: Aug. 1, 2017

(54) KIT FOR PREPARATION OF TARGET RADIOPHARMACEUTICALS AND METHOD OF USING IT

(71) Applicant: Institute of Nuclear Energy Research Atomic Energy Council, Executive Yuan, Taoyuan County (TW)

(72) Inventors: Shu-Pei Chiu, Taoyuan County (TW); Bo-Sian Lin, Taipei (TW); Liang-Ting Lin, Taipei (TW); Yi-Jang Lee, Taipei (TW); Te-Wei Lee, Taipei (TW); Feng-Yun Huang, Hualien County (TW); Jem-Mau Lo, Hsinchu County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 280 days.

(21) Appl. No.: 14/531,127

(22) Filed: Nov. 3, 2014

(65) Prior Publication Data
US 2016/0114061 A1    Apr. 28, 2016

(30) Foreign Application Priority Data

Oct. 23, 2014   (TW) .............................. 103136665 A

(51) Int. Cl.
*A61K 51/00* (2006.01)
*A61K 51/12* (2006.01)
*A61K 51/06* (2006.01)
*A61J 1/05* (2006.01)

(52) U.S. Cl.
CPC ............... *A61K 51/065* (2013.01); *A61J 1/05* (2013.01); *A61K 51/1234* (2013.01); *A61K 51/1237* (2013.01)

(58) Field of Classification Search
CPC ........ A61K 51/00; A61K 51/04; A61K 5/106; A61K 51/12; A61K 5/06
See application file for complete search history.

(56) References Cited

U.S. PATENT DOCUMENTS

| 7,718,160 B2 * | 5/2010 | Bao ....................... C07F 13/005 424/1.11 |
| 2008/0226546 A1 * | 9/2008 | Lee ...................... A61K 31/704 424/1.21 |

OTHER PUBLICATIONS

Phillips et al., "Rhenium-186 liposomes as convectionenhanced nanoparticle brachytherapy for treatment of glioblastoma", Neuro-Oncology 14(4):416-425, Jan. 2012.
French et al., "Interventional Therapy of Head and Neck Cancer with Lipid Nanoparticle-Carried Rhenium-186 Radionuclide", J Vasc Intery Radiol; 21(8): 1271-1279,Aug. 2010.

* cited by examiner

*Primary Examiner* — Michael G Hartley
*Assistant Examiner* — Jagadishwar Samala
(74) *Attorney, Agent, or Firm* — WPAT, PC; Justin King; Douglas A. Hosack

(57) ABSTRACT

The invention relates to a kit for preparation of target radiopharmaceuticals, a method of using the kit to prepare target radiopharmaceuticals and use of the target radiopharmaceuticals. The target radiopharmaceuticals comprise a radio-nuclear loading on liposome and inhibit the tumor growth and metastatic progression of head and neck cancer, lung cancer and brain cancer. The radiopharmaceuticals may be used for treating the mentioned cancers.

3 Claims, 4 Drawing Sheets

(A) (B)

(A)            (B)

(A)        (B)

US 9,717,808 B2

KIT FOR PREPARATION OF TARGET RADIOPHARMACEUTICALS AND METHOD OF USING IT

FIELD OF THE INVENTION

The invention relates to a kit for preparation of target radiopharmaceuticals, a method of using the kit to prepare target radiopharmaceuticals and use of the target radiopharmaceuticals. The target radiopharmaceuticals comprise a radio-nuclear loading on liposome and inhibit the tumor growth and metastatic progression of head and neck cancer, lung cancer and brain cancer.

BACKGROUND OF THE INVENTION

It is known that tumor cells grow fast if they are supplied with nutrients by angiogenesis. However, tumor cells growth during angiogenesis will result in vascular hypoplasia, which in turn results in a lot of leakages in micrometer order on blood vessels. Such a loose structure of blood vessels allows drug penetrate into tumor cells cavity easily. Moreover, since tumor tissue lacks of normal lymphatic network, if drugs enter into tumor cells, it is very difficult to leave through normal lymphoid tissue so that it could prolong residence time of drugs in tumor cells, which is so-called Enhanced Permeability and Retention (EPR) effect. Due to such a property, drugs in a size of from 100 nm~200 nm is considered be a potential for treating tumor.

Liposomes were first discovered by Alec Bangham, a British scientist, in 1960s. Liposomes are a spherical vesicle composed of a lamellar phase lipid bilayer, which structure is similar to the composition of cell membrane. Liposomes are biocompatible and biodegradable in human body. Liposomes comprise phospholipid, which phosphate end is hydrophilic and lipid end is hydrophobic so that liposomes can be used as a carrier both for hydrophobic and hydrophilic drug. Particle size of liposomes is from tens nanometers (nm) to tens micrometers (μm), they do not easily enter into the blood vessels in normal tissue, since the gaps between normal vascular endothelial cells are closed. However, since the gaps between tumor endothelial cells are enough large to yield the EPR effect, liposomes easily enter tumor endothelial cells and accumulate on tumor sites, thus improve the therapy efficiency of the drug carried on them. Thus, if therapeutic radionuclides are encapsulated in liposomes, it could improve tumor therapeutic effects of β-ray emitted by radionuclides. Methods for labeling radioisotopes onto liposomes are generally divided into two ways. One is a surface labeling method, which comprises directly labeling radionuclides on liposome on which surface bonded with chelators. Another is an embedding (after loading) method, which is the most common method. For example, Bao et al. published that N,N-bis(2-mercaptoethyl)-N',N'-diethylethylenediamine (BMEDA) labeled with rhenium-188 (Re-188), rhenium-186 (Re-186) and technetium-99m were embedded in liposome and studied its effect on radiotherapy and imaging agents of radiodiagnosis on normal mice (Bao et al. J. Pharm. Sci (2003) 92, 1893-1904; J. Nucl. Med (2003), 44, 1992-1999; U.S. Pat. No. 7,718,160 B2). The common features in the after loading methods for preparing radiolabeled liposomes are: (i) Radioisotopes require the helps of chelators or ionophores to enter into liposomes. Therefore, a step of labeling of chelators with radioisotopes is necessary in this process. (ii) After entering into liposomes, radioisotopes need to react with other chelators or buffers solution to remain within liposomes stably. But there are disadvantages in using the after loading methods for preparing radiolabeled liposomes: (i) The used chelator, i.e. BMEDA is liquid state, it is easy oxidized so that the efficiency labeling with Re-186 or Tc-99m will be reduced. (ii) Additional purifying steps are required because of the low loading efficiency (generally the loading efficiency is about 60% to about 80%). (iii) The kit is un-stable for long time storage so that it should be prepared just before use. Furthermore, the whole labeling process is complex and time-consuming, it will reduce the radioactivity of radiopharmaceuticals to be prepared (for example, Re-188 radionuclides, which half-life is about 16.9 hours) so that the kinds of radioisotopes which can be used are limited.

There are many researches about therapy efficiency of Re-188 or Re-186-radiolabeled liposomes for treating colon cancer, head and neck cancer and breast cancer. In 2010, French et al. studied interventional therapy effect of head and neck cancer with $^{186}$Re-liposome (185 MBq (5 mCi)/cm$^3$ tumor) (J Vasc Interv Radiol. 2010; 21(8): 1271-1279) and reported that average tumor volume of the $^{186}$Re-Liposome group on post-treatment day-14 was decreased to 87.7±20.1% (<0.001) and radiation absorbed dose on tumor was 526.3±93.3 Gy, which is far higher than $^{186}$Re-perrhenate and $^{186}$Re-BMEDA groups. And no systemic toxicity was observed. In 2012, Phillips et al. used $^{186}$Re-Liposome for treatment of glioblastoma at a dose of up to 1850 Gy by local injection and no overt clinical or microscopic evidence of toxicity was found (Neuro-Oncology 2012; 14(4):416-425). Animals treated with $^{186}$Re-Liposomes in a dose of 1850Gy had a median survival of 126 days (95% confidence interval [CI], 78.4-173 days), while control group is 49 days (95% CI, 44-53 days). And no systemic toxicity was observed. Although it showed that $^{186}$Re-Liposome is effective to treat the head and neck cancer and glioblastoma, the administration is limited to local injection, which will limit $^{186}$Re-Liposome to only use in the treatment of carcinoma in situ, and cannot be used in treatment of metastatic cancer.

Comparing with rhenium-186, rhenium-188 is a carry free and can be obtained in high radioactivity from tungsten-188 generator, thus it is more convenient for clinical use. Further, the half-life of rhenium-188 is 16.9 hr which is shorter than rhenium-186 (its half-life is 90 hr), thus rhenium-188 is safer and can use lower dose in clinical use.

SUMMARY OF THE INVENTION

In view of the above, the present invention relates to a system for preparation of target radiopharmaceuticals, a method of using the kit to prepare target radiopharmaceuticals and use of the target radiopharmaceuticals. By using $^{188}$Re as a radionuclide embedded in liposomes through BMEDA chelator to produce $^{188}$Re-Liposomes can avoid the reticuloendothelial system (RES) and pass through the vascular slit in lively angiogenesis for passive target drug accumulating in tissues by the mechanism of EPR (enhanced permeability and retention) effect.

The main object of the present invention is to provide a system for preparation of target pharmaceuticals, which comprises: (1) vial A which contains lyophilized mixture of N,N-bis(2-mercaptoethyl)-N',N'-diethyl-ethylenediamine (BMEDA), sodium gluconate, and stannous chloride; (2) vial B which contains an aqueous solution of radionuclide including $^{188}$Re and/or $^{186}$Re; and (3) vial C which contains an aqueous liposome solution comprising phospholipid, cholesterol, and 1,2-distearoyl-sn-glycero-3-phosphoethanolamine-N-[maleimide(polyethyleneglycol)-2000] (DSPE-PEG$_{2000}$) in a mole ratio of 30~95:20~45:3~7.5.

In the present kit, the phospholipid is 1,2-distearoyl-sn-glycero-3-phosphocholine (DSPC) or hydrogenated soybean phosphatidylcholine.

In the present kit, the mole ratio of BMEDA, sodium gluconate, and stannous chloride in vial A is BMEDA: sodium gluconate:stannous chloride=10:2~100:1~40.

In the present kit, the specific activity of $^{188}$Re and/or $^{186}$Re is 1 mCi~100 mCi/mL.

In the present kit, the volume ratio of vial A and vial C is 1:1~1:10.

In the present kit, the aqueous solution in vial B and C are both saline solution.

Another object of the present invention is to provide a method of using the present kit to prepare target radiopharmaceuticals, which comprises the steps of: (1) injecting the solution in the vial B into the vial A and reacting at an appropriate temperature for appropriate period; (2) adjusting the pH of the mixture obtained in step (1) in a range of 6~7 by adding aqueous sodium hydroxide solution, and (3) injecting the liposome solution in the vial C into the vial A obtained in step (2) and reacting at an appropriate temperature for an appropriate period to obtain target pharmaceutical, i.e $^{188}$Re- and/or $^{186}$Re-Liposome.

In the present method, the step (1) is carried out in a temperature of from 4° C.~110° C. for 30 minutes to 75 minutes.

In the present method, the step (3) is carried out in a temperature of from 4° C.~80° C. for 15 minutes to 60 minutes.

Further object of the present invention is to provide a target pharmaceutical, which is prepared by the present method, which is liposome labeled with $^{188}$Re- and/or $^{186}$Re through chelator BMEDA (hereinafter, it is called as $^{188}$Re- and/or $^{186}$Re-Liposome).

Rhenium-188 ($^{188}$Re) is a radionuclide having a short half-life of 16.9 hours and emitting 155 keV γ emission suitable for imaging and 2.12 MeV β emission suitable for treating tumor. Therefore, in clinical use, a patent can first be administered with a low dose, for example, 3~14 mCi of "$^{188}$Re- and/or $^{186}$Re-Liposome" to evaluate the size and position of tumor, then be administered with a high dose, for example more than 14 mCi for treatment, so that "$^{188}$Re- and/or $^{186}$Re-Liposome" possess both functions of treatment and diagnostic of tumor.

The present target pharmaceutical, i.e. $^{188}$Re- and/or $^{186}$Re-Liposome is useful for treatment of head and neck cancer, lung cancer, brain cancer and their metastatic. Advantages of the present kit are follows: (1) easy use, (2) simple operation, (3) high purity without further purification; (4) suitable for clinical use; and (5) possess both functions of treatment and diagnostic of tumor.

DETAILED DESCRIPTION OF THE INVENTION

Figure 1:
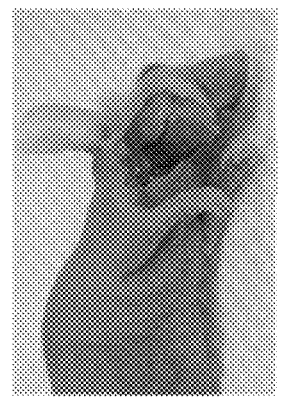
FIG. 1 shows photographs of a mouse implanting with FaDu-GLT cells to establish head and neck cancer (FIG. 1(a)) and its bioluminescent image photograph (FIG. 1(b)).
Figure 1:
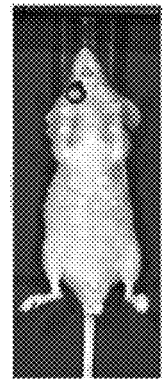

The present invention will be illustrated by the followings, which are merely for example without limiting the scope of the present invention.

The following abbreviations are employed:
BMEDA: N,N-bis(2-mercaptoethyl)-N',N'-diethylethylenediamine
DSPC: Distearoyl phosphatidylcholine
PEG: Polyethylene glycol

EXAMPLE 1

The Preparation of Lyophilized Mixture of N,N-Bis (2-Mercaptoethyl)-N',N'-Diethyl-Ethylenediamine (BMEDA), Sodium Gluconate, and Stannous Chloride Vial A 148 mg sodium gluconate were dissolved in 1 mL 10% acetic acid solution to obtain an aqueous sodium gluconate solution and 20 mg stannous chloride were dissolved in 2 mL 0.1N HCl to obtain an aqueous stannous chloride solution. Then 35 mg BMEDA, 875 μL of the sodium gluconate solution and 840 μL of the stannous chloride solution were pipetted into a fresh vial, then flushing with nitrogen gas for 2 minute to avoid the oxygenation of stannous chloride to obtain a mixture containing BMEDA, sodium gluconate and stannous chloride. The resultant mixture solution was split charged into each vials in an amount of 152 μL/vial, which contains BMEDA/sodium gluconate/stannous chloride=3.08 mg/77.1 μL/74.1 μL (mole ratio of 1:4:0.3). Then these vials were subjected to a lyophilized process. The conditions of lyophilized process are described in Table 1.

TABLE 1

Condition of the lyophilized process

| lyophilized process | Step | Time | Temperature | Pressure |
| --- | --- | --- | --- | --- |
| Pre-frozen | 1 | 1 hr | −80° C. | <0.120 mBar |
| Primary lyophilized | 2 | 36 hr | −80° C. | <0.120 mBar |
| Second lyophilized | 3 | 12 hr | 18° C. | <0.120 mBar |

Upon finishing the lyophilized process, each vials was flushed with $N_2$ gas, sealed and stored in −20° C., which is corresponding to vial A.

EXAMPLE 2

Preparation of Vial C

DSPC (55.31 g, 70 μmole), cholesterol (18.14 g, 46.66 μmole), and DSPE-PEG2000 (20.59 g, 7 μmole) (mole ratio of 30:20:3) were weighted into a 200 mL round bottom and added with 8 mL choloform to dissolve them thoroughly. The resultant mixture was evaporated by using rotary evaporators at 60° C. to remove solvent and thus a lipid film was formed on the wall of the flask. Then 5 mL of 250 mM ammonium sulfate solution (250 mM $(NH_4)_2SO_4$, pH 5.0, 530 mOs) were added into the flask and the flask was shaken in a water bath at 60° C. until the lipid film was dispersed in ammonium sulfate solution thoroughly to obtain multi-layer liposome (MLV) dispersion. The multi-layer liposome dispersion was frozen in liquid nitrogen and de-frozen in water bath at 60° C. with repeating six times. Then the multi-layer liposome dispersion was extruded by high pressure film extruder (Lipex Biomembrane, Vancouver, Canada) to obtain single two-layer liposome. The resultant two-layer liposome dispersion was loaded on Sephadex G50 gel permeation column and purified by using 0.9% NaCl solution as a eluent. The eluted fraction was collected and determined its particle size by using nano-ZX (Malvern, UK.) to be a normal distribution in a range of from 80~120 nm. Using Bartlett's Method to determine the phospholipid concentration in the liposome is found to be 13~14 μmole/mL.

EXAMPLE 3

Preparation of $^{188}$Re-Liposome

A $^{188}$ReO$_4^-$ solution (vial B) added into vial A in a radioactivity of 4 mCi/mL, and the resultant mixtures reacted at 80° C. for 60 minutes. 55 uL 2N NaOH were added to the vial A to adjust the pH of the mixture to 6. The labeling reaction is as follows.

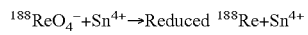

$^{188}$ReO$_4^-$+Sn$^{4+}$→Reduced $^{188}$Re+Sn$^{4+}$

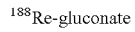

$^{188}$Re-gluconate

Reduced $^{188}$Re+gluconate→

$^{188}$Re-gluconate+2BMEDA→$^{188}$Re(BMEDA)$_2$+gluconate

Then an aqueous liposome solution in vial C into the above vial A (having added with the solution in vial B) in a volume ratio of vial A to vial C of 1:1). The resultant mixtures reacted in 60° C. for 30 minutes. Completing the reaction, the vial was cold down at room temperature to obtain a target radiopharmaceutical, i.e. $^{188}$Re-Liposome. The encapsulating efficiency of the $^{188}$Re-Liposome was determined by PD-10 column (GE Healthcare) with using normal saline as the eluent. The PD-10 column was first conditioned with 20 mL normal saline, then loaded with 100 μL $^{188}$Re-Liposome and eluted with saline. The eluted solution was collected in each tube in an amount of 0.5 ml/tube for total 20 tubes. The encapsulating efficiency of $^{188}$Re-Liposome was calculated according to the following standard formula:

The encapsulating efficiency (%)=[100%×(Rhenium-188 main peak activity/(Total radioactive)].

Wherein total radioactive: the sum of total fraction radioactivity and column residue.

Rhenium-188 main peak activity: the sum of Radioactivity of fractions with $^{188}$Re-Liposome (fraction5-10).

A purification is not required if the encapsulating efficiency exceeds 90%.

TABLE 2 the labeling yield and encapsulating efficiency in different radioactive.

| No. | Radioactive of $^{188}$Re (mCi/mL) | Labeling yield (%) | Encapsulating efficiency (%) |
|---|---|---|---|
| 1 | 4.01 | 100 | 93.32 |
| 2 | 5.02 | 100 | 93.54 |
| 3 | 6.59 | 100 | 90.83 |
| 4 | 9.03 | 100 | 92.51 |

EXAMPLE 4

Therapeutic Efficacy Studies of $^{188}$Re-Liposome Treatment in Human HNSCC Mice Model The FaDu-GLT cells were implanted into BALB/c nude mice at a concentration of $10^6$ cells/50 μl to to establish head and neck cancer. 16 days after implantation, the mice were obverted by naked eye and by bioluminescent imaging. FIG. 1 shows photographs of a mouse implanting with FaDu-GLT cells to establish head and neck cancer (FIG. 1(a)) and its bioluminescent image photograph (FIG. 1(b)).

Figure 2:
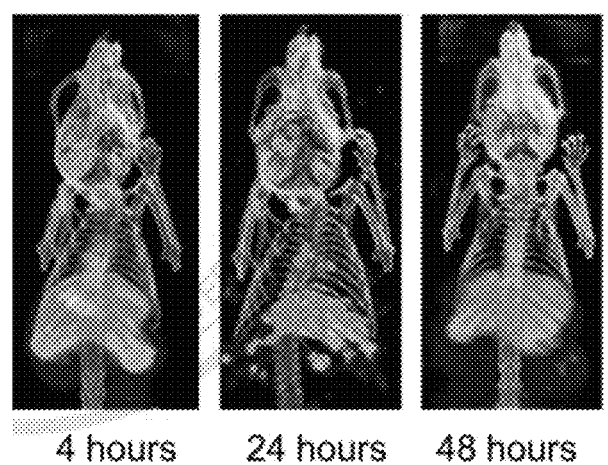
FIG. 2 shows SPECT/CT imaging photographs of the mouse suffering head and neck cancer at 4, 24, and 48 hours after administration of present $^{188}$Re-Liposome.
Figure 3:
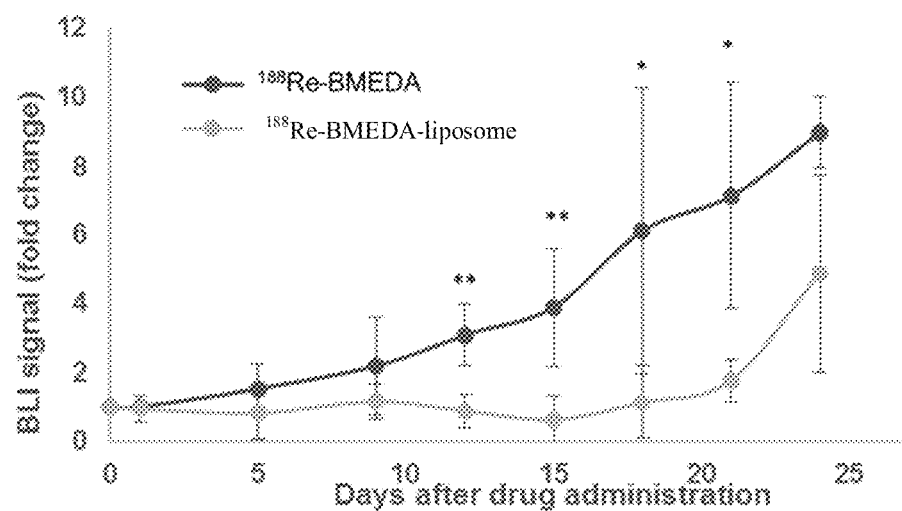
FIG. 3 shows a graph of strength of bioluminescence in tumor administrating with $^{188}$Re-BMEDA and $^{188}$Re-Liposome, respectively.

The $^{188}$Re-BMEDA and $^{188}$Re-Liposome were separately injected intravenously into tumor-bearing mice with 640 μCi in a single dose, each group has 9 BALB/c nude mice. The mice of $^{188}$Re-Liposome group were imaged at 4, 24, and 48 hours after administration which SPECT/CT imaging photographs were shown in FIG. 2. The reconstructed 3D nanoSPECT/CT image showed a clear signal in the lower oral cavity. Moreover, the bioluminescent image signal revealed that the tumor growth was repressed within 15 days after $^{188}$Re-Liposome administration (FIG. 3).

EXAMPLE 5

Clinical Study of $^{188}$Re-Liposome in Patients with Metastatic Cancer

Each patient with metastatic cancer receives single dose 3 mCi $^{188}$Re-Liposome injection. After $^{188}$Re-Liposome administration, single-photon emission computed tomography (SPECT) imaging were carried out on 1, 4, 8, 24, 48 and 72 hours, and computed tomography (CT) were carried out on 24 hours. Image registration was conducted by Velocity AI imaging software for the SPECT images each time point with the CT image of 24 hour to evaluate biodistribution and radiation dosimetry on normal organs and tumor.

Figure 4:
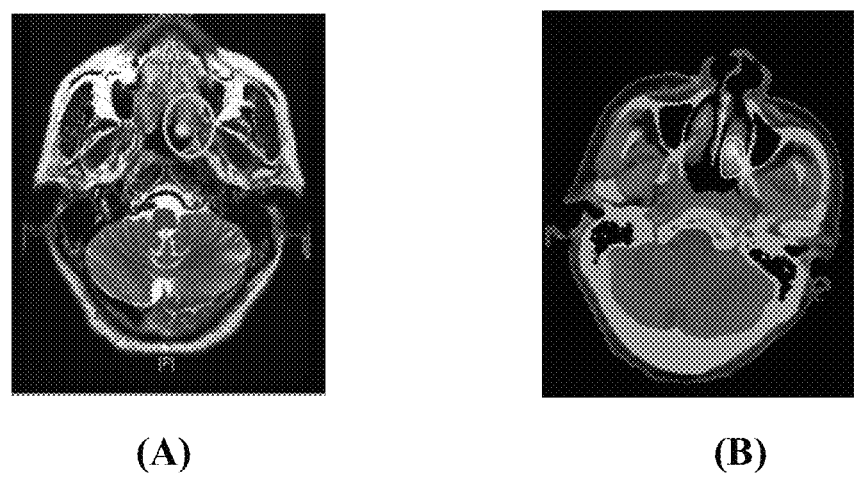
FIG. 4 shows MRI imaging photographs of a patent suffering with head and neck metastases before administration of $^{188}$Re-Liposome (FIG. 4(a)) and SPECT/CT imaging photographs after administration of $^{188}$Re-Liposome (FIG. 4(b)).
Figure 5:
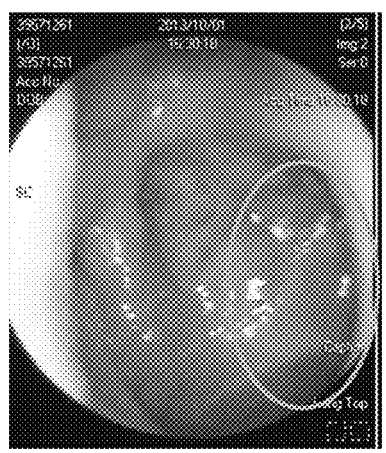
FIG. 5 shows nasopharynx endoscopic photographs of a patent suffering with head and neck metastases before (FIG. 5(a)) and after (FIG. 5(b)) administration of $^{188}$Re-Liposome.
Figure 5:
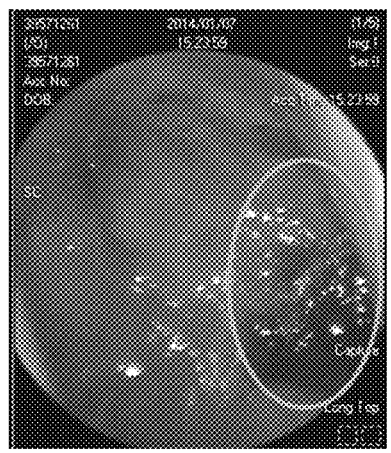

One of the patients suffering head and neck metastases received $^{188}$Re-Liposome and subjected to SPECT and CT imaging. The MRI image was acquired for tumor diagnosis about one month before this study, and a nasopharyngeal tumor in left nasal cavity was observed (FIG. 4(a)). The SPECT/CT fusion image on 24 hour revealed that $^{188}$Re-liposome distributes at the same location with MRI image (FIG. 4(b)). In addition, from nasopharynx endoscopic examination results, it shown that the lesion has engorged blood vessels and irregular surface over left nasopharynx one month before $^{188}$Re-Liposome administration (FIG. 5(a)), but it has been in regression with much crust and mucoid over nasopharynx two month after $^{188}$Re-Liposome injection (FIG. 5(b)).

EXAMPLE 6

Figure 6:
FIG. 6 shows tumor growth photographs for BALB/c nude mice implanting with H292-GLT cell to establish small cell lung cancer via microCT (FIG. 6(a)) and bioluminescent imaging (FIG. 6(b)).
Figure 6:
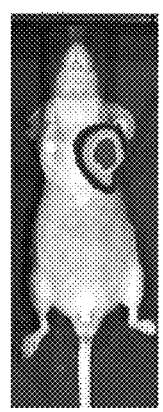

Therapeutic Efficacy Studies of $^{188}$Re-Liposome Treatment in Human NSCLC Mice Model A centimeter incision was made on the left chest wall of nude mice to precisely locate the insertion of needle, and $10^6$ H292-GLT cells were injected through 29-gauge syringe in a mixture with Matrigel. 16 days after the intrapulmonary implantation of human NSCLC, the solid tumor was also visible in the coronal view of microCT image (FIG. 6(a)). Moreover, the bioluminescent imaging (BLI) which is a crucial tool for quantifying the growth of tumors was assessed by the In Vivo Imaging System (IVIS) with the administration of D-luciferin (FIG. 6(b)).

The $^{188}$Re-BMEDA and $^{188}$Re-Liposome were separately injected intravenously into tumor-bearing mice with 640 µCi in a single dose, each group has 9 BALB/c nude mice.

The survival was recorded since the first mice died from the treatment or the disease up to 60 days. Median survival time (Table 3) exhibited a significant difference between these two groups, the result of $^{188}$Re-BMEDA group is 26 days, and the $^{188}$Re-Liposome group is 40 days.

Figure 7:
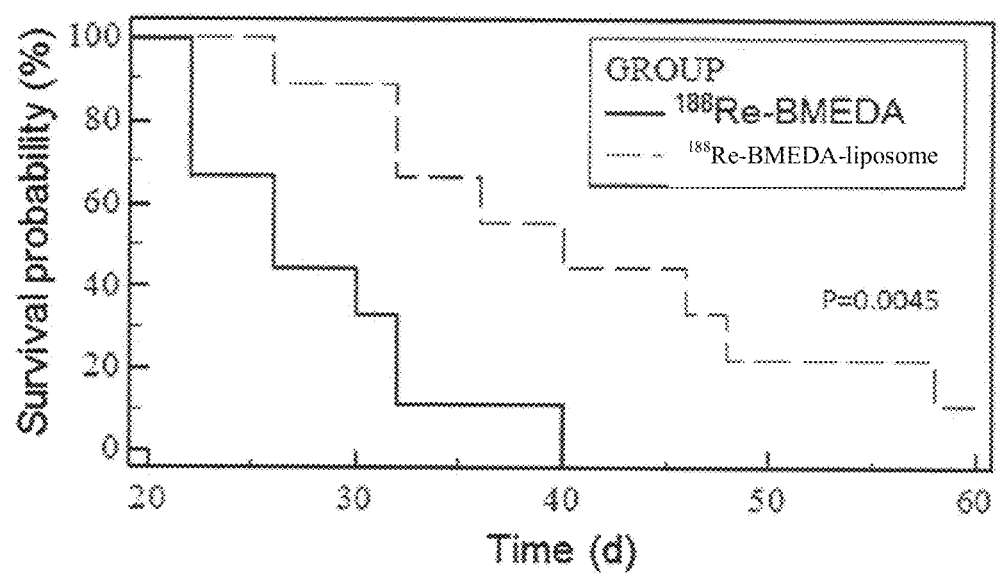
FIG. 7 shows a Kaplan-Meier survival curve of $^{188}$Re-BMEDA treated group and $^{188}$Re-Liposome treated group.
Figure 8:
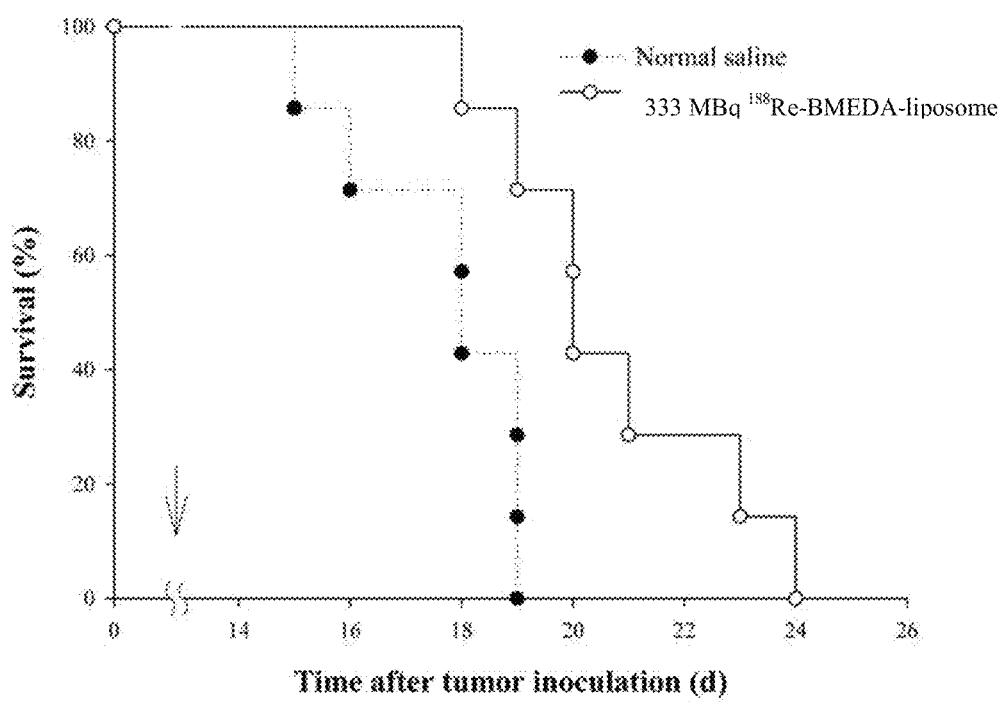
FIG. 8 shows a Kapla-Meier survival curves of Fischer 344/F98$_{luc}$ orthotopic glioma bearing rat model after single intravenous injection of normal saline (●) and 333 MBq $^{188}$Re-Liposome (○), respectively (n=7).

The Kaplan-Meier survival curves (FIG. 7) showed mice given $^{188}$Re-Liposome was observed after 60 days and still 10% survival, whereas $^{188}$Re-BMEDA mice are all died on 40 days.

TABLE 3 median survival time analysis of $^{188}$Re-BMEDA group and $^{188}$Re-Liposome group

|  | $^{188}$Re-BMEDA | $^{188}$Re-Liposome |
|---|---|---|
| Sample size(n) | 9 | 9 |
| Median survival (days) | 26 | 40 |
| significance | P = 0.0045 | |
| 95% CI | 0.1131 to 0.9615 | |

EXAMPLE 7

Therapeutic Efficacy Studies of $^{188}$Re-Liposome Treatment in Human NSCLC Mice Model The rats (male, 12-13 week old) were anesthetized with Isofluorane® and then administered with atropine sulfate (0.1 mg/kg) via subcutaneous injection; subsequently, the rats were deeply anesthetized by intraperitoneal injection of Zoletil® 50 and Balanzine 2% mixture at a 5:2 volume ratio (0.1 mL/100 g rat body weight). After anesthesia, the rat head's hair on operative field was removed. Then, the rats were immobilized by a stereotactic frame (Stoelting®, USA). A 2 cm linear incision was carefully operated and the field-open immobilized for the following surgery. After removing the periosteum, a 1 mm diameter of hole was created with a high-speed drill at the right brain (located at 3 mm lateral to midline and 5 mm anterior to lambda) and the dura carefully pricked with a sharp tweezers. For implantation, the $F98_{luc}$ cells were harvested and re-suspended in Hanks' balanced salt solution (HBSS) plating on the ice before use. The $1\times10^5$ cells in 10 µL medium were inoculated into the brain (a depth of 5 mm from the skull bone) using a 100 µL Hamilton® syringe and 27½ gauge needle through nanoliter syringe pump (KDS 310 plus; Holliston, Mass., USA) with the injection rate at 3 µL/min. After seeding, the needle was retained for 2 min and then drawn out carefully and slowly. Finally, paraffin was used to fill the surgical hole and the incision was sutured. The rats were observed closely until completely awakening.

To evaluate therapeutic efficacy of $^{188}$Re-Liposome in Fischer344/$F98_{luc}$ orthotopic glioma bearing rat model, 35 rats in total were used herein. For survival evaluation study, fourteen tumor bearing rats were randomly divided into two groups (seven rats per groups). Subsequently, the rats of two groups were administered with normal saline (control group) and $^{188}$Re-Liposome (333 MBq/0.5 mL; 2.5 µmol phospholipid/0.5 mL) via single intravenous injection on Day 7 post-inoculation, respectively. Then the rats were monitored for survival and body weight every day until death. The survival curves for treating with $^{188}$Re-Liposome and normal saline in Fischer344/$F98_{luc}$ glioma-bearing rat model. The result revealed that the lifespan for $^{188}$Re-Liposome was significantly increased as 10.67% compared to control group (P=0.007). The statistical analysis for therapeutic efficacy evaluation is summarized in Table 4. The maximum survival time for $^{188}$Re-Liposome and control groups was 24 and 19 days, respectively. In addition, the median survival time was 20.75 and 18.75 days, respectively.

TABLE 4

Therapeutic efficacy evaluation of 333-MBq $^{188}$Re-Liposome in orthotopic glioma-bearing rat model.

| njection | No. of rat/group | Dose (MBq) | Maximum survival time (d) | Median survival time (d) | Prolongation in lifespan (%) | P-value |
|---|---|---|---|---|---|---|
| $^{188}$Re-Liposome | 7 | 333 | 24 | 20.75 | 10.67 | 0.007 |
| Normal saline | 7 | None | 19 | 18.75 | — | — |

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

What is claimed is:

1. A method for preparing target radiopharmaceuticals, which comprises the steps of:
   (1) mixing a vial B and a vial A and reacting the same at an appropriate temperature for an appropriate period, wherein the vial A contains lyophilized mixture of N,N-bis(2-mercaptoethyl)-N',N'-diethyl-ethylenediamine(BMEDA), sodium gluconate, and stannous chloride, and the vial B contains an aqueous solution of radionuclide including $^{188}$Re and/or $^{186}$Re lyophilized, and wherein the lyophilized mixture is prepared by the steps of:
   a) mixing BMEDA, sodium gluconate, and stannous chloride to produce a mixture;
   b) freezing the mixture at −80° C. and flushing the same with N$_2$ gas under 0.120 mBar for 1 hour;
   c) lyophilizing the mixture at −80° C. and flushing the same with N$_2$ gas under 0.120 mBar for 36 hours; and
   c) lyophilizing the mixture at 18° C. and flushing the same with N$_2$ gas under the pressure of 0.120 mBar for 12 hours;
   (2) adjusting the pH of the mixture obtained in step (1) in a range of 6~7 by adding aqueous sodium hydroxide solution, and
   (3) injecting the liposome solution in a vial C into the mixture obtained in step (2) and reacting at an appropriate temperature for an appropriate period to obtain a target pharmaceutical, i.e., $^{188}$Re-and/or $^{186}$Re-Liposome, wherein the vial C contains an aqueous liposome solution comprising phospholipid, cholesterol, and 1,2-distearoyl-sn-glycero-3-phosphoethanolamine-N-[maleimide (polyethylene glycol)-2000] (DSPE-PEG 2000) in a mole ratio of 30~95:20~45:3~7.5.

2. The method according to claim 1, wherein the step (1) is carried out in a temperature of from 4° C.~110° C. for 30 minutes to 75 minutes.

3. The method according to claim 1, the step (3) is carried out in a temperature of from 4° C.~80° C. for 15 minutes to 60 minutes.

* * * * *